United States Patent
Genger et al.

(10) Patent No.: US 8,204,584 B2
(45) Date of Patent: *Jun. 19, 2012

(54) DEVICE FOR DETECTING ELECTRICAL POTENTIALS OF THE FOREHEAD REGION OF A PATIENT

(75) Inventors: Harald Genger, Starnberg (DE); Claus Negele, München (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/914,488

(22) Filed: Oct. 28, 2010

(65) Prior Publication Data

US 2011/0041851 A1   Feb. 24, 2011

Related U.S. Application Data

(63) Continuation of application No. 11/311,862, filed on Dec. 19, 2005, now Pat. No. 7,848,794, which is a continuation of application No. 09/980,573, filed as application No. PCT/EP00/03997 on May 4, 2000, now Pat. No. 7,054,680.

(30) Foreign Application Priority Data

May 4, 1999 (DE) ................................. 199 20 433
Aug. 5, 1999 (DE) ................................. 199 36 505
Oct. 8, 1999 (DE) ................................. 299 17 806 U
Nov. 26, 1999 (DE) ................................. 199 56 841

(51) Int. Cl.
*A61B 5/04* (2006.01)
*A62B 18/02* (2006.01)

(52) U.S. Cl. ....................................... 600/544

(58) Field of Classification Search ............. 128/206.21; 600/300, 372, 382, 383, 386, 388, 390, 391, 600/393, 529, 544, 545

See application file for complete search history.

(56) References Cited

U.S. PATENT DOCUMENTS

| | | | |
|---|---|---|---|
| 3,706,308 A * | 12/1972 | John et al. | 600/483 |
| 5,406,957 A | 4/1995 | Tansey | |
| 5,479,934 A * | 1/1996 | Imran | 600/544 |
| 5,657,752 A | 8/1997 | Landis et al. | |
| 5,687,717 A | 11/1997 | Halpern et al. | |
| 5,755,230 A | 5/1998 | Schmidt et al. | |
| 6,000,395 A * | 12/1999 | Brown | 128/202.19 |
| 6,167,298 A | 12/2000 | Levin | |
| 6,171,258 B1 | 1/2001 | Karakasoglu et al. | |
| 6,199,550 B1 | 3/2001 | Wiesmann et al. | |
| 6,230,049 B1 | 5/2001 | Fischell et al. | |
| 6,272,378 B1 | 8/2001 | Baumgart-Schmitt | |
| 7,848,794 B2 * | 12/2010 | Genger et al. | 600/544 |

FOREIGN PATENT DOCUMENTS

DE   21 06 552   8/1972

(Continued)

*Primary Examiner* — Max Hindenburg
*Assistant Examiner* — Jonathan M Foreman
(74) *Attorney, Agent, or Firm* — Nixon & Vanderhye P.C.

(57) ABSTRACT

A device for detecting electrical potentials in the forehead area of a patient has a transverse member adapted to rest against the forehead of the patient, a vertical member extending crosswise to the transverse member and a mask on the vertical member. Electrodes are provided on the transverse members at least at its ends and at the center at which the vertical bar crosses the transverse member.

18 Claims, 4 Drawing Sheets

FOREIGN PATENT DOCUMENTS

| | | |
|---|---|---|
| DE | 692 31 157 | 11/1991 |
| DE | 695 01 327 | 3/1994 |
| DE | 94 00 950 | 10/1995 |
| DE | 696 34 262 | 10/1995 |
| DE | 94 18 874 | 11/1995 |
| DE | 298 16 662 | 2/1999 |
| EP | 0 815 792 | 6/1997 |
| WO | WO 97/10019 | 3/1997 |
| WO | WO 97/16216 | 5/1997 |
| WO | WO 98/12965 | 4/1998 |

* cited by examiner

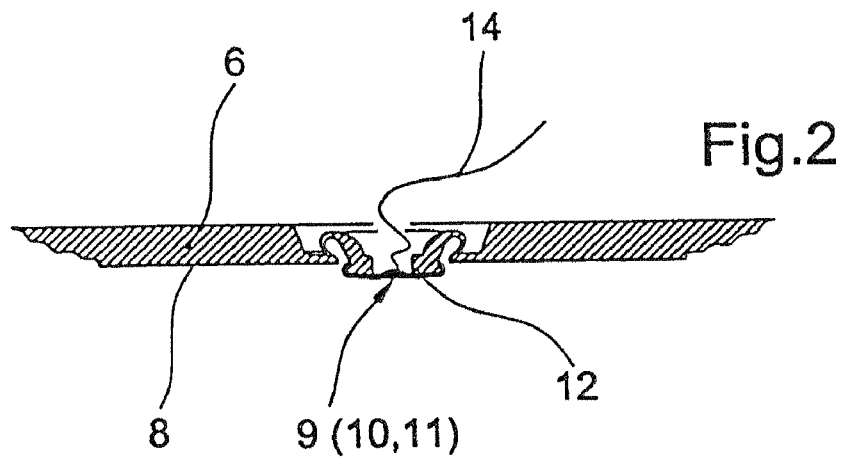
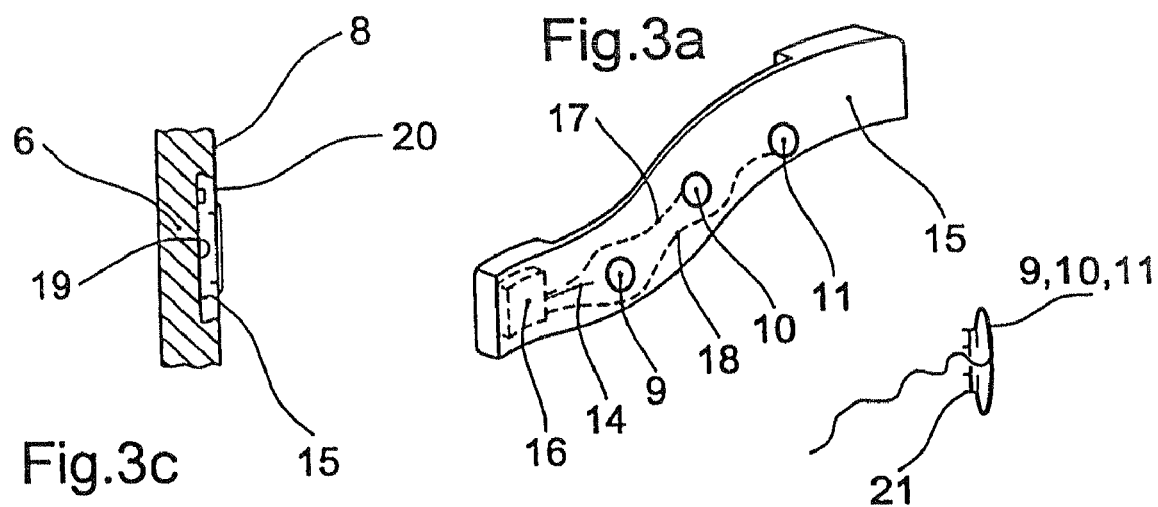
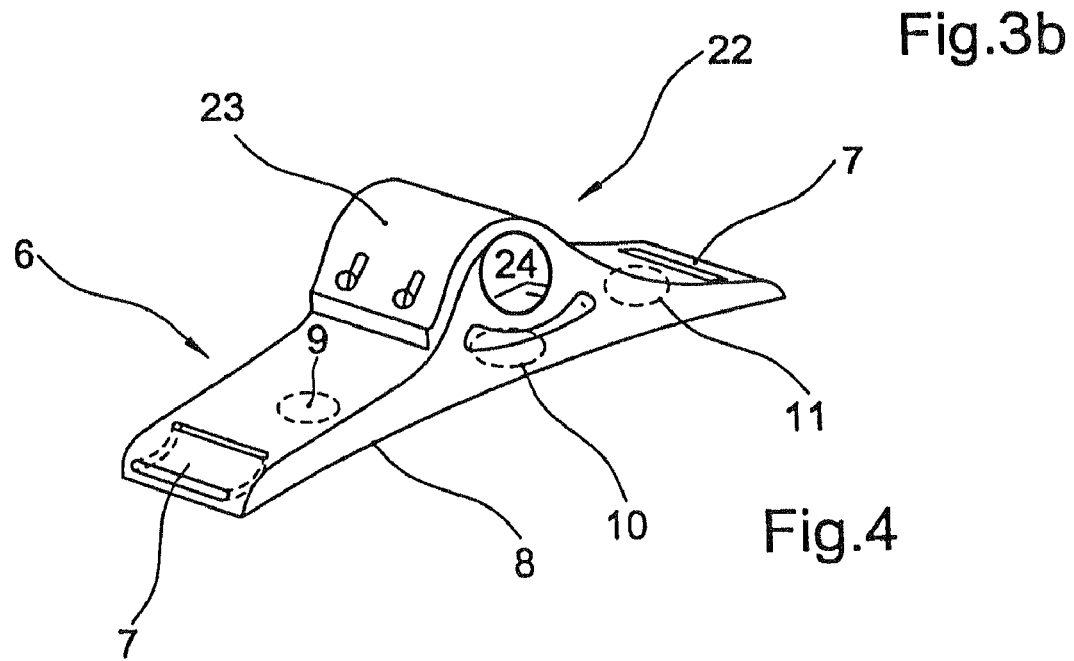

Fig.5
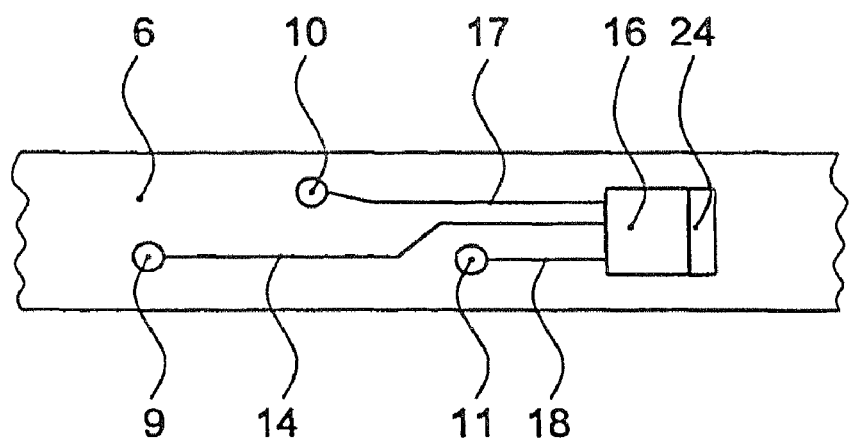
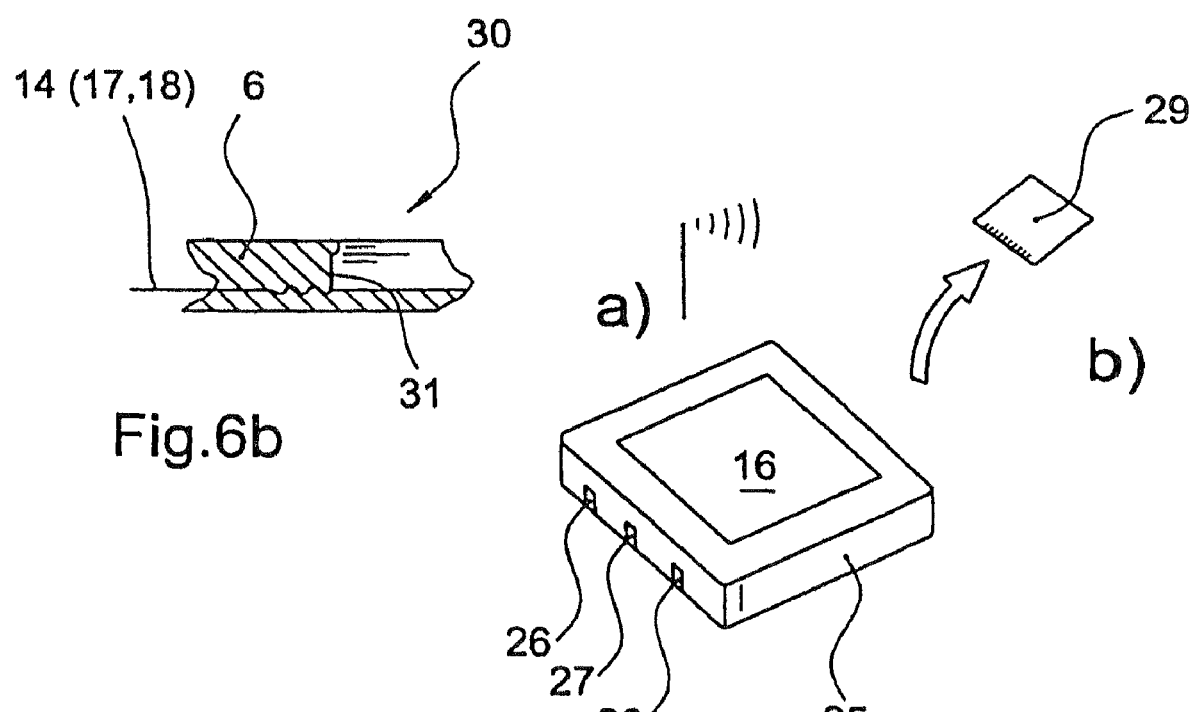
Fig.6b
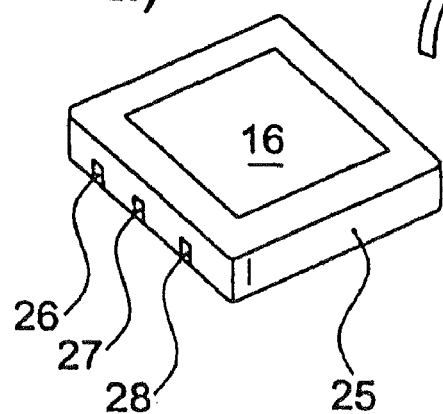
Fig.6a

DEVICE FOR DETECTING ELECTRICAL POTENTIALS OF THE FOREHEAD REGION OF A PATIENT

CROSS-REFERENCES TO RELATED APPLICATIONS

This application is a continuation of U.S. application Ser. No. 11/311,862, filed 19 Dec. 2005, now allowed, which is a continuation of U.S. application Ser. No. 09/980,573, now U.S. Pat. No. 7,054,680, filed 6 Feb. 2002 as a national stage of PCT/EP00/03997 filed 4 May 2000 and based upon German National applications 199 20 433.0 of 4 May 1999, 199 36 505.9 of 5 Aug. 1999, 299 17 806.4 filed 8 Oct. 1999, and 199 56 841.3 filed 26 Nov. 1999 under the International Convention.

FIELD OF THE INVENTION

The invention relates to a device for detecting electrical potentials in the forehead region of a patient.

BACKGROUND OF THE INVENTION

It is possible, on the basis of electrical potentials to draw conclusions about the brain activity of a human being. In particular, it is possible, in the case of a person who is asleep, to determine the individual sleep states, on the basis of the brain activity which is ascertained during sleep.

German patent application DE 199 20 433.0 to the present applicants describes a CPAP device system in which the characteristic of the respiration gas feed is varied in dependence on the sleep state of the patient. For that purpose, the required electrodes are glued onto the forehead of the patient by way of an adhesive strip.

The correct application of such electrodes requires particular care and is frequently found to be unpleasant by the patient in question.

OBJECT OF THE INVENTION

The object of the invention is to improve the reliability of detection of electrical potentials in the forehead region of a patient and to permit application of the required electrodes in a manner which is agreeable to the patient.

SUMMARY OF THE INVENTION

In accordance with the invention that object is attained by a device for detecting electrical potentials on a patient, with an electrode device which can be applied in the forehead region of the patient, wherein the electrode device is arranged on a forehead support element which co-operates with a breathing mask device in such a way that the application position of the electrode device is established in conjunction with the application position of the breathing mask device.

That makes it advantageously possible to apply the electrode device in the correct position, with a high level of reproduction accuracy.

In accordance with a particularly preferred embodiment of the invention the forehead support element is coupled to the breathing mask device. In that arrangement, the electrode device can advantageously be directly applied to and removed from the breathing mask arrangement. It is possible to forego the adhesive strips which were hitherto required, which is an advantage.

A particularly high level of adaptability of the forehead support element to the individual configuration of the forehead part of the patient and a high degree of wearing comfort is afforded, in accordance with a particularly preferred embodiment of the invention, by virtue of the forehead support element being formed from an elastomer material.

An embodiment of the invention which in particular saves weight and which is advantageous from hygiene points of view is afforded if the forehead support element is formed in one piece with a mask base member of the breathing mask device.

In accordance with a particular aspect of the present invention the spatial configuration of the unit formed from the forehead support element and the mask member can be adapted to the individual contour of the face of the patient by the provision of a stiffening element which stiffeningly couples together the forehead support element and the breathing mask device.

The electrode device preferably includes at least two electrode elements, the potential difference being detected between those two electrode elements. Considerably more accurate determination of the electrical brain activity of the patient is made possible by the electrode device having at least three electrode elements. The electrode elements are placed for example in the frontal measurement locations fP1 and fP2 and a location therebetween. Preferably the measurement locations are disposed in the forehead region of the patient about 30 mm above the eyebrows.

A particularly high level of measuring accuracy is advantageously achieved if the electrode elements are supported flexibly in a direction substantially perpendicular to the application face. That ensures that for example the arrangement does not give rise to electrode contact pressure forces which are different in dependence on a forehead band tension. For that purpose for example the electrode elements are accommodated in a cup structure. The flexible effect can be achieved by elastomer elements, in particular rolling bellow diaphragms. As an alternative thereto it is also possible for the electrode elements to be accommodated in a recess, the depth of the recess substantially corresponding to the thickness of the electrode elements.

In accordance with a particularly preferred embodiment of the invention the electrode elements are coupled to a signal processing device arranged in the immediate proximity of the electrode elements. For that purpose the signal processing device is particularly advantageously integrated into the forehead support element and has its own voltage supply device, for example in the form of a button cell. The output of the signal processing device is preferably potential-free and communicates directly with a data transmission device for cordless and in particular radio transmission of the processed signals to a data processing device. It is possible for the potentials detected by way of the electrode elements also to be processed in the region of the forehead support element by means of a suitable data processing device so that a compressed or more informative data set is produced which can be forwarded at a lower level of transmission complication and expenditure. On the other hand it is also possible to forward substantially only the raw data, that is to say the measurement results, to a separate receiving device.

That receiving device can be part of a patient monitoring system of a sleep laboratory. It is also possible for the receiving device to be integrated directly into a CPAP device. Particularly in the case of that embodiment, it is also possible, in place of telemetric signal transmission, to provide a data line which is particularly advantageously integrated into a breathing gas hose.

Particularly in regard to the area of use of sleep therapy for treating sleep-related respiratory disturbances the above-specified object is also attained by a breathing mask arrangement for feeding a respiration gas to a patient under an increased pressure, comprising a mask member which engages over the nose region of the patient, a sealing device for sealing off an inner region of the mask with respect to the ambient atmosphere, and a forehead support element for supporting the mask member in the forehead region of the patient, characterized in that provided in the region of the forehead support element is an electrode device for detecting electrical and in particular brain-electrical potentials.

In that respect the forehead support element, as already described in greater detail hereinbefore, is also preferably formed from an elastomer material and is either produced integrally with the mask member or is coupled thereto in a defined manner by way of a suitable joining structure.

Particularly when the forehead support element and the mask member involve an integral design configuration, it is also formed from an elastomer material. Particularly in this embodiment, the forehead support element and the mask member are provided with stiffening or bracing means which extend into the forehead support element, the stiffening means preferably being adapted to the individual face contour of the patient.

In combination with the above-described features or also alternatively thereto, the above-specified object is also attained by a device for detecting electrical potentials in the forehead region of a patient, in particular for determining sleep stages, comprising an electrode device, a measuring circuit arrangement for producing measurement data in accordance with the electrical potentials detected by the electrode device, wherein the measuring circuit arrangement is integrated into a forehead support element, and there is provided a signal transmission device for cord-less transmission of the measurement data produced by the measuring circuit arrangement.

The measuring circuit arrangement preferably has a data compression device for transmitting a compressed data set to the signal transmission device.

In accordance with the invention, the foregoing object is attained in an advantageous fashion in accordance with a further aspect of the present invention by a device for detecting electrical potentials in the forehead region of a patient, in particular for determining sleep stages, comprising an electrode device, a measuring circuit arrangement for producing measurement data in accordance with the electrical potentials detected by the electrode device, wherein the measuring circuit arrangement is integrated into a forehead support element, and there is provided a measurement data recording device for recording the measurement data produced by the measuring circuit arrangement.

In a particularly advantageous manner that measurement data recording device includes an approximately postage stamp-size memory card element which is releasably coupled to the forehead support element and which can be removed for example from the forehead support element for further processing of the recorded items of information. The measurement data can possibly be compressed by a compression device provided in the region of the forehead support element.

BRIEF DESCRIPTION OF THE DRAWINGS

Further details will be apparent from the description hereinafter of a number of preferred embodiments of the invention and detail structures which are advantageously embodied in that respect, with reference to the accompanying drawing in which:

FIG. 2 is a cross sectional view which shows an elastically yielding mounting of an electrode element, FIG. 3a is a perspective view of an elastomer band element which has three electrodes for detecting the electrical brain activity of a patient, wherein the band element can be coupled to a forehead support element, FIG. 3b is a simplified sectional view through a forehead support element into which the band element shown in FIG. 3a is fitted, FIG. 3c is a simplified sectional view through an electrode element as is used in particular in the forehead support element shown in FIG. 3a, FIG. 4 is a perspective view of a further embodiment of a forehead support element with integrated electrode elements for detecting the electrical brain activity of a patient, wherein the forehead support element can be coupled to a duct portion of a breathing mask, FIG. 5 is a simplified diagram to illustrate a forehead band element with integrated signal processing device, FIG. 6a is a perspective view of a signal processing device provided for use in a forehead support element, either in case a for telemetric data transmission (for example by radio) or case b for the storage of a preferably compressed data set on an interchangeable data carrier, preferably in chip card form, FIG. 6b is a simplified sectional view through a receiving portion in a forehead support element for receiving the signal processing device shown in FIG. 6a, and FIG. 7 is a simplified perspective view of a measuring arrangement according to the invention for detecting the electrical brain activity of a patient here with a total of five electrode elements pre-positioned by way of a breathing mask and a telemetric data transmission device.

DETAILED DESCRIPTION OF THE INVENTION

Figure 1:
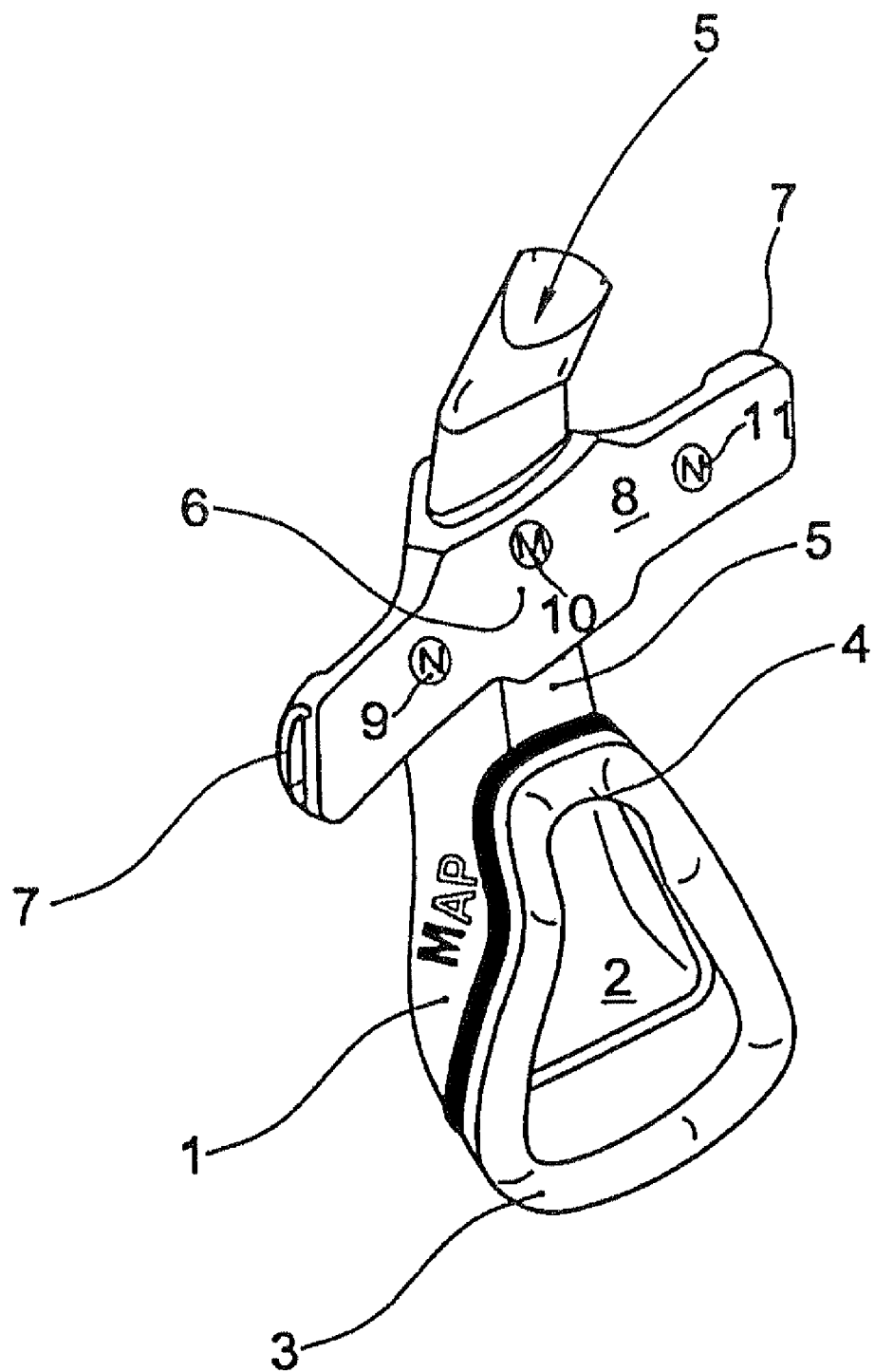
FIG. 1 is a perspective view which shows a perspective view of a breathing mask with a forehead support element which has three electrodes for detecting electrical potentials in the forehead region of the patient.

The breathing mask shown in FIG. 1 includes a mask member 1 which delimits an internal space 2 of the mask. Provided on an edge portion which is towards the ambient region of the nose of a patient is a sealing device 3 which here has at least one elastic sealing lip which comes into intimate contact with the surface of the face of the patient and in so doing seals off the internal space 2 of the mask with respect to the ambient atmosphere. Here, the sealing device 3 has a portion 4 which is drawn in comparatively deeply in the region of the bridge of the nose, thereby affording placement of the mask member 1 with respect to the nose of the patient, in such a way that it remains the same with a high degree of accuracy of repetition.

In the embodiment illustrated here the mask member 1 has a breathing gas duct 5 which extends through a forehead support element 6. The gas duct 5 is a stiffening element which stiffeningly couples the forehead support element 6 to the mask 1. In the embodiment illustrated here, the mask member 1 and the forehead support element 6 are formed integrally from an elastomer material, in particular a fully transparent silicone rubber material.

In the illustrated embodiment, the forehead support element 6 is provided with connecting members 7 by way of which the forehead support element 6 can be coupled to a preferably cushioned forehead band. In the illustrated embodiment, the contact surface 8 of the forehead support element 6, which faces towards the forehead of the patient, is of a slightly concave configuration and in addition is adapted by a stiffening element (not shown here) to the individual contour of the forehead region of the patient, in terms of the curvature thereof. In the illustrated embodiment arranged in the contact surface 8 are a total of three electrode elements 9, 10 and 11, by way of which it is possible to detect electrical potentials in the forehead region of the patient. The forehead support element 6 is transverse to the tubular member 5 and has free ends on opposite sides of a central portion, an electrode 9, 11 being on each end and the other electrode 10 being on the central portion.

The position of the electrode elements 9, 10, 11 relative to the patient can be maintained with high level of accuracy of repetition as the unit formed by the mask member 1 and the forehead support element 6 is fixed precisely, in particular by the nose region of the patient.

In the embodiment illustrated here, the breathing gas duct 5 is of a non-round and in particular polygonal cross-section and in addition is of a configuration such as to curve towards the patient, corresponding to the curvature of the forehead of the patient. The cross-sectional shape used here provides that the breathing gas flows into the internal space 2 of the mask in a substantially eddy-free flow. That measure represents an independent novel structural configuration of the invention for improving the breathing gas flow which can also be implemented on its own account, independently of the features otherwise described herein.

Referring to FIG. 2, shown therein is a simplified diagrammatic view illustrating a preferred embodiment of the mounting of the electrode elements 9, 10, 11 as are used in the breathing mask shown in FIG. 1. As can be seen, the electrode elements 9, 10, 11 are formed by a thin metal plate 12 which is mounted yieldingly substantially perpendicularly to the contact surface 8. The yielding mounting is achieved in this case by a diaphragm structure which is formed integrally with the forehead support element 6. Provided in the rearward region of the metal plate 12 is a highly flexible metal line device 14 which will be described hereinafter in an embodiment which is described in greater detail with reference to FIGS. 3*a* and 5. The elastically yielding mounting for the electrode elements 9, 10 and 11 as shown in FIG. 2, provides that the electrode elements are urged against the surface of the skin of the patient with a contact pressure force which remains substantially the same, thereby avoiding possibly falsified measurement results as a consequence of different forces in the forehead band arrangement.

FIG. 3*a* shows a particular embodiment of the electrode arrangement according to the invention, which here has a band 15 which is formed from an elastomer material and into which the electrode elements 9, 10 and 11 are fitted. The band 15 is of an outside contour which permits positionally accurate coupling to a forehead support element. Fitted in an end portion of the band 15 is a signal processing device 16 which is connected by way of thin connecting lines 14, 17 and 18 to the respective electrode elements 9, 10 and 11.

The potential differences between the respective electrode elements are detected and evaluated in that signal processing device. The measurement data obtained in that way are either stored in suitably encoded form or passed by telemetric means to a receiving device for further data processing.

FIG. 3*c* is a sectional view through a portion of a forehead support element 6 into which is fitted the band 15 referred to in reference to FIG. 3*a*. For that purpose a recess 19 is provided in the forehead support element 6. The depth of the recess 19, which is set back with respect to the contact surface 8, is such that the contact surface 20 formed by the band 15 terminates substantially flush with the contact surface 8.

The electrode elements 9, 10 and 11 are mounted on the band 15, as already indicated in FIG. 3*a*.

As indicated in FIG. 3*b* for example the electrode elements can be fixed by the electrode elements having on their rear side needle-like projections 21, by way of which the electrode elements can be individually placed on the band 15 or directly on the forehead support element 6.

As an alternative thereto it is also possible to form shallow recesses in the forehead support element 6 or in the band 15. The shallow recesses are delimited by a peripheral edge into which the electrode elements 9, and 11 can be clipped, by means of a slight clipping fit.

FIG. 4 shows a perspective view of a forehead support element 6 which can be coupled to a breathing gas duct portion of a breathing mask. For that purpose the forehead support element 6 has a mask fixing portion 22. The mask fixing portion, in the embodiment illustrated here, includes a flexible band 23 defining a through passage 24 for receiving the breathing gas duct 5.

The forehead support element 6 also has connecting members 7 which—as already indicated with reference to FIG. 1—serve for the further connection of a forehead band. The electrode elements 9, 10 and 11 are again fitted in the region of the contact surface 8 of the forehead support element 6. The electrode elements 9, 10 and 11 can be repeatably applied in an accurate position in the forehead region of the corresponding patient, as a consequence of the breathing mask being coupled to the forehead support element 6.

FIG. 5 indicates in a simplified manner the fashion in which the individual electrode elements 9, 10 and 11 are coupled to the signal processing device 16 by way of the connecting lines 14, 17 and 18. In this case, the signal processing device 16 includes a directly connected data transmission device 24 by way of which the measurement data obtained can be cordlessly forwarded to a suitable system for further processing. In the embodiment illustrated here, all of the specified components are sealingly embedded in the base member of the forehead support element 6, the base member being formed from an elastomer material.

FIG. 6*a* shows a particularly preferred embodiment of the signal processing device 16 which is here accommodated in an outer casing 25 and has a plurality of contact elements 26, 27 and 28 which can be electrically connected to the connecting lines 14, 17 and 18 referred to in connection with FIG. 5. The processing device 16 illustrated here includes its own voltage supply device formed by a button cell (not shown) and, in dependence on the potential differences detected between the contacts elements 26, 27 and 28, produces binary-coded data. Those data can be transmitted to an external data processing system, as indicated for case a, in the form of electromagnetic waves, in particular by radio. As an alternative thereto or also in combination therewith, it is possible—as indicated for case b—for the measurement data obtained to be stored on a data carrier 29. In order to obtain direct association in respect of time of said measurement data, the signal processing device 16, in accordance with a particularly preferred embodiment of the invention, can be provided with a clock so that the measurement data produced are also stored in accordance with an association in respect of time.

The signal processing device 16 which is in the form of a completely self-contained block can be clipped—as indicated in FIG. 6*b*—into a recess 30 which is clipped directly in the forehead support element 6 or as indicated for example in the case shown in FIG. 3*a* into a suitable band 15. In that case, by virtue of the inherent elasticity of the material surrounding the recess 30, the contact elements 26, 27 and 28 on the signal processing device 16 come into a sufficiently high pressing contact relationship with the further co-operating contacts 31 provided in the forehead support element 6. Those co-operating contacts 31 are connected to the above-mentioned signal lines 14, 17 and 18.

Figure 7:
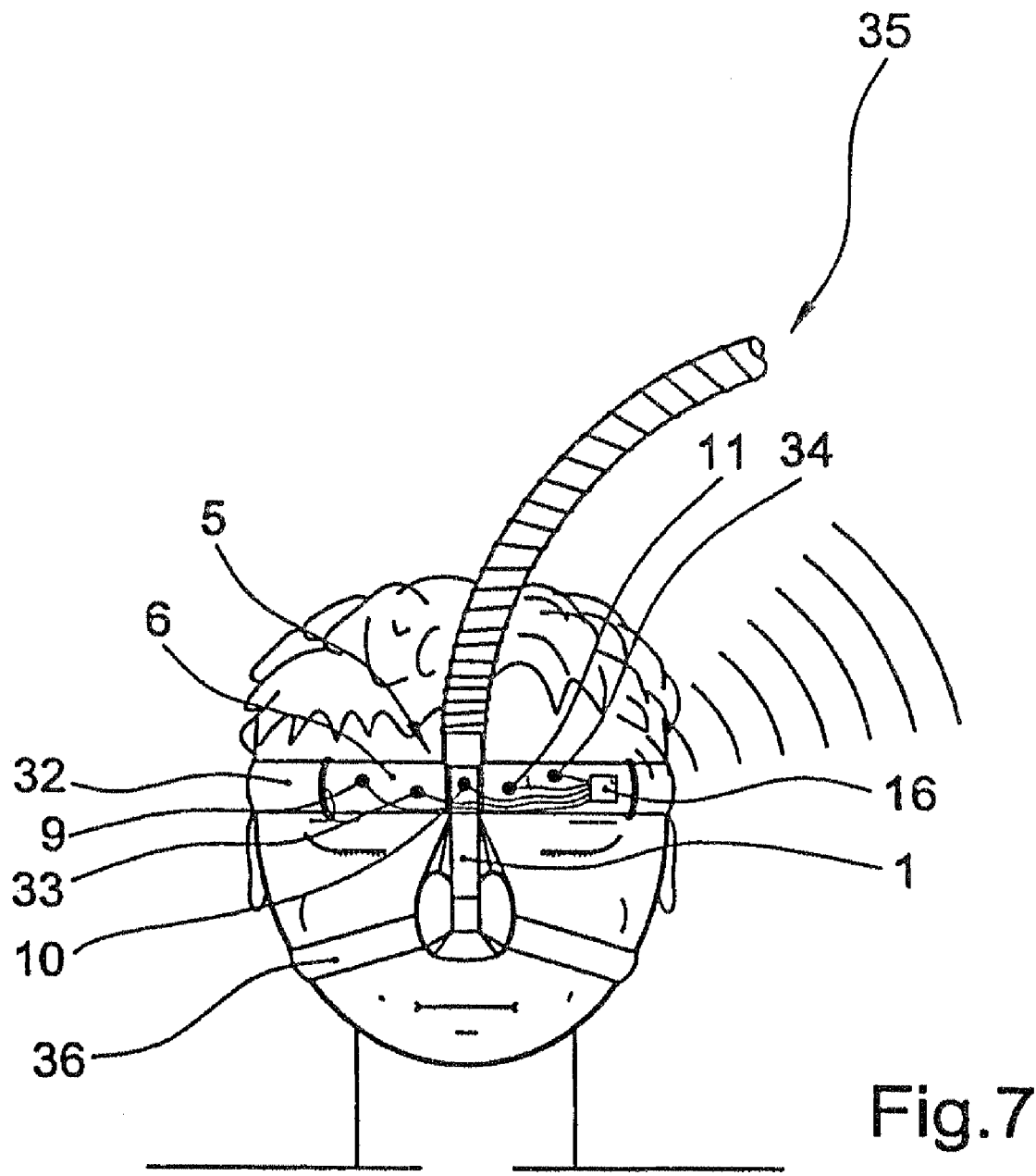

FIG. 7 shows in a simplified fashion the way in which a breathing mask according to the invention with integrated forehead electrodes is applied in the face region of a patient. It will be clear in that respect that extremely precise positioning of the electrode elements is achieved by virtue of the coupling in accordance with the invention of the electrode elements to a forehead support element which is provided to support a breathing mask. That arrangement makes it possible for a plurality of electrode elements, in particular as shown here five electrode elements, to be applied in the forehead region of the patient, in which case upon fresh application of the electrode elements substantially the same measurement position is again employed as in the case of the preceding measurement procedures. That provides for considerably improved comparability of the data obtained in the context of different measurement cycles.

The measuring arrangement shown in FIG. 7 includes the mask member 1 and the forehead support element 6 which is coupled thereto by way of the breathing gas duct portion 5 and which is only indicated here. Arranged in the forehead support element 6 in this case are a total of five electrodes 9, 10, 11 and 33 and 34 by way of which it is possible to detect electrical potential differences in the forehead region of the patient.

The potential differences detected in that way are evaluated by the signal processing device 16 integrated in the forehead support element 6 and forwarded by way of radio signals to an external receiving device for further processing and in particular for the control of a CPAP unit.

In this case, the feed of respiration gas to the internal space of the mask, which is defined by the mask member 1, is by way of a breathing gas hose 35 provided with a reinforcing insert of spiral configuration.

Particularly in the case of a breathing gas hose of that kind, it is possible to provide that the signals are transmitted by means of a line device which is integrated into the breathing gas hose 35, in particular in the spiral reinforcing member thereof, instead of the signals produced by the signal processing device 16 being transmitted by way of radio.

The region of the mask member which is adjacent to the mouth of the patient, is urged against the face of the patient with a predetermined contact pressure force, by a lower webbing band arrangement 36. The forehead support element 6 is urged against the forehead of the patient with an adjustable contact pressure force by an upper webbing band arrangement 32 which extends around the region of the back of the head of the patient. Both the lower band arrangement 36 and also the upper band arrangement 32 in the embodiment illustrated here are formed by a cushioned band material which is comparatively resistant to tensile force. The high level of resistance to tensile force of that band material provides that, even when the breathing mask is applied to the face of the patient with comparatively low levels of contact pressure force, the breathing mask does not lift away from the face of the patient, as a consequence of the increased pressure which obtains in the inside of the mask. In the region of the coupling location between the breathing gas hose 35 and the breathing gas duct portion 5 of the breathing mask it is optionally possible to provide a ball joint device which still further suppresses the application of any turning moments to the breathing mask.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A CPAP device capable of varying a characteristic of a respiratory gas feed in accordance with an apparatus for detecting electrical potentials in the forehead region of a patient, the apparatus comprising:
    a patient interface adapted to communicate with the airways of the patient in use; and
    an electrode device provided to the patient interface and having at least two electrode elements directly engagable with the forehead region to detect electrical potentials,
    a measuring circuit that produces measurement data in accordance with the electrical potentials detected by the electrode device, wherein the measuring circuit is integrated into a forehead support element that is self-locating relative to the patient's forehead region in use by virtue of fitting the patient interface to the patient, and
    a measurement data recorder that records the measurement data produced by the measuring circuit.

2. An apparatus according to claim 1, further comprising a breathing gas duct connected to the patient interface, wherein the forehead support element is connected to the breathing gas duct.

3. An apparatus according to claim 2, wherein the breathing gas duct extends through the forehead support element.

4. An apparatus according to claim 1, wherein the measuring circuit is provided in a recess of the forehead support element and contacts of the measuring circuit contact co-operating contacts in the recess.

5. An apparatus according to claim 1, comprising three electrode elements, wherein two electrode elements are provided at respective ends of the forehead support element and the third electrode element is provided in a middle portion of the forehead support element.

6. An apparatus according to claim 1, wherein the measuring circuit comprises a clock that determines a time at which measurement data is produced.

7. An apparatus according to claim 1 wherein the measuring circuit is provided in a band which is fitted in the forehead support element.

8. An apparatus according to claim 6, wherein the at least two electrode elements are provided in the band.

9. An apparatus according to claim 1, wherein the at least two electrode elements are elastically mounted to the forehead support element.

10. A CPAP device capable of varying a characteristic of a respiratory gas feed in accordance with an apparatus for detecting electrical potentials in the forehead region of a patient, the apparatus comprising:
    means for feeding respiration gas to the airways of the patient; and
    means provided to the patient interface and directly engagable with the forehead region for detecting electrical potentials,
    means for producing measurement data in accordance with the detected electrical potentials, wherein the measurement data producing means is integrated into a forehead support element that is self-locating relative to the patient's forehead region in use by virtue of fitting the respiration gas feeding means to the patient, and means for recording the measurement data produced by the measurement data producing means.

11. An apparatus according to claim 10, further comprising a breathing gas duct connected to the respiration gas feeding means, wherein the forehead support element is connected to the breathing gas duct.

12. An apparatus according to claim 11, wherein the breathing gas duct extends through the forehead support element.

13. An apparatus according to claim 10, wherein the measurement data producing means is provided in a recess of the forehead support element and contacts of the measurement data producing means contact co-operating contacts in the recess.

14. An apparatus according to claim 10, wherein the electrical potential detecting means comprises three electrical potential detecting means, wherein two electrical potential detecting means are provided at respective ends of the forehead support element and the third electrical potential detecting means is provided in a middle portion of the forehead support element.

15. An apparatus according to claim 10, wherein the measurement data producing means comprises a means for determining a time at which measurement data is produced.

16. An apparatus according to claim 10, wherein the measurement data producing means is provided in a band which is fitted in the forehead support element.

17. An apparatus according to claim 16, wherein the electrical potential detecting means is provided in the band.

18. An apparatus according to claim 10, wherein the electrical potential detecting means is elastically mounted to the forehead support element.

* * * * *